US010280308B2

(12) United States Patent
Dietz et al.

(10) Patent No.: US 10,280,308 B2
(45) Date of Patent: May 7, 2019

(54) EFFECT PIGMENTS

(71) Applicant: MERCK PATENT GMBH, Darmstadt (DE)

(72) Inventors: Johann Dietz, Dietzenbach (DE); Cornelia Foerderer, Heppenheim (DE); Nicole Haferkorn, Pfungstadt (DE); Gerhard Pfaff, Muenster (DE); Doreen McFarlane, Bickenbach (DE)

(73) Assignee: MERCK PATENT GMBH, Darmstadt (DE)

(*) Notice: Subject to any disclaimer, the term of this patent is extended or adjusted under 35 U.S.C. 154(b) by 0 days.

(21) Appl. No.: 15/127,292

(22) PCT Filed: Mar. 11, 2015

(86) PCT No.: PCT/EP2015/000536
§ 371 (c)(1),
(2) Date: Sep. 19, 2016

(87) PCT Pub. No.: WO2015/139825
PCT Pub. Date: Sep. 24, 2015

(65) Prior Publication Data
US 2017/0130054 A1 May 11, 2017

(30) Foreign Application Priority Data
Mar. 20, 2014 (DE) .......... 10 2014 003 975

(51) Int. Cl.
A61K 8/02 (2006.01)
A61K 8/26 (2006.01)
A61K 8/29 (2006.01)
C08K 9/02 (2006.01)
C09C 1/00 (2006.01)
C09C 1/40 (2006.01)
C09D 17/00 (2006.01)
A61Q 1/02 (2006.01)
C09D 5/28 (2006.01)
C09D 5/36 (2006.01)
C09D 7/40 (2018.01)
C09D 11/037 (2014.01)

(52) U.S. Cl.
CPC .......... C09C 1/0024 (2013.01); A61K 8/0262 (2013.01); A61K 8/26 (2013.01); A61K 8/29 (2013.01); A61Q 1/02 (2013.01); C08K 9/02 (2013.01); C09C 1/407 (2013.01); C09D 5/28 (2013.01); C09D 5/36 (2013.01); C09D 7/40 (2018.01); C09D 7/70 (2018.01); C09D 11/037 (2013.01); C09D 17/008 (2013.01); A61K 2800/412 (2013.01); A61K 2800/621 (2013.01); C01P 2004/20 (2013.01); C01P 2004/51 (2013.01); C01P 2004/54 (2013.01); C01P 2004/61 (2013.01); C01P 2004/86 (2013.01); C01P 2006/60 (2013.01); C09C 2200/1004 (2013.01); C09C 2200/301 (2013.01); C09C 2200/302 (2013.01); C09C 2200/306 (2013.01); C09C 2220/106 (2013.01)

(58) Field of Classification Search
None
See application file for complete search history.

(56) References Cited

U.S. PATENT DOCUMENTS

| 4,867,793 | A | 9/1989 | Franz et al. | |
| 5,322,561 | A * | 6/1994 | Prengel .................. | B82Y 30/00 106/415 |
| 5,972,098 | A | 10/1999 | Andes et al. | |
| 2003/0092815 | A1 | 5/2003 | Steudel et al. | |
| 2004/0244640 | A1* | 12/2004 | Vogt ......................... | A61K 8/26 106/31.9 |
| 2007/0028799 | A1* | 2/2007 | Kniess .................. | C09C 1/0015 106/31.6 |
| 2008/0279796 | A1 | 11/2008 | Handrosch | |
| 2010/0075031 | A1* | 3/2010 | Bujard ................. | C01G 23/053 427/215 |
| 2011/0226161 | A1 | 9/2011 | Schumacher | |
| 2013/0164356 | A1 | 6/2013 | Pfaff | |

(Continued)

FOREIGN PATENT DOCUMENTS

CN 1575323 A 2/2005
CN 101289580 A 10/2008
(Continued)

OTHER PUBLICATIONS

J Patzlaff, M Rosier. "Sparkle Effects in Thin Layers." European Coatings Jounal. Issue Jan. 2, 2006, p. 56, 3 printed pages. Downloaded by examiner from http://www.european-coatings.com/content/download/61088/701812/version/1/file/55354.pdf on Oct. 17, 2017. Originally published in 2006. (Year: 2006).*
International Search Report dated Jan. 29, 2015, issued in corresponding PCT/EP2014/075850, 3 pages.
English translation Abstract of EP0246523B1 published Jan. 9, 1991 (1 page).
English translation Abstract of WO9743348A1 published Nov. 20, 1997 (1 page).

(Continued)

Primary Examiner — Isaac Shomer
(74) Attorney, Agent, or Firm — Millen White Zelano and Branigan, PC; John Sopp

(57) ABSTRACT

The present invention relates to silver-colored effect pigments having a strong sparkle effect based on Al2O3 flakes and to the use thereof in paints, button pastes, automotive paints, automotive refinish paints, powder coatings, printing inks, security printing inks, plastics, ceramic materials, glasses, paper, for coating seed, in security applications, as dopant for the laser marking of plastics and papers, as additive for the laser welding of plastics, in cosmetic formulations and for the preparation of pigment preparations and dry preparations.

23 Claims, No Drawings

(56) References Cited

U.S. PATENT DOCUMENTS

| | | |
|---|---|---|
| 2014/0010772 A1 | 1/2014 | Gruner et al. |
| 2014/0322536 A1 | 10/2014 | Suzuki |
| 2016/0185972 A1 | 6/2016 | Schmidt |

FOREIGN PATENT DOCUMENTS

| | | |
|---|---|---|
| CN | 103459515 A | 12/2013 |
| CN | 104130598 A | 11/2014 |
| CN | 104870571 A | 8/2015 |
| DE | 19618563 A1 | 11/1997 |
| EP | 0246523 B1 | 1/1991 |
| EP | 0681009 A2 | 11/1995 |
| EP | 2502966 A1 | 9/2012 |
| JP | 2005-075941 A | 3/2005 |
| JP | 2008-214634 A | 9/2008 |
| JP | 2010-502774 A | 1/2010 |
| JP | 2013-502468 A | 1/2013 |
| JP | 2013-129831 A | 7/2013 |
| WO | 97/43348 A1 | 11/1997 |
| WO | 01/77235 A1 | 10/2001 |
| WO | 2004/099319 A2 | 11/2004 |
| WO | 2008/026829 A1 | 3/2008 |
| WO | 2012/130776 A | 10/2012 |

OTHER PUBLICATIONS

English translation Abstract of DE19618563A1 published Nov. 13, 1997 (1 page).
English translation Abstract of WO2004099319A2 published Nov. 18, 2004 (1 page).
English translation Abstract of EP2502966A1 published Sep. 26, 2012 (1 page).
English translation Abstract of WO2012130776A1 published Oct. 4, 2012 (1 page).
English translation Abstract of EP0681009A2 published Nov. 8, 1995 (1 page).
English translation Abstract of JP2005075941A published Mar. 24, 2005 (1 page).
English translation Abstract of WO0177235 published Oct. 18, 2001 (1 page).
Chinese Office Action corresponding to CN 2015/80014622.2, dated Nov. 23, 2017.
Office Action in corresponding application JP 2016-558071 dated Oct. 16, 2018 (pp. 1-5).

* cited by examiner

EFFECT PIGMENTS

The invention relates to silver-coloured effect pigments having a strong sparkle effect based on $Al_2O_3$ flakes which have two highly refractive layers and to the use thereof, in particular, in paints, coatings, printing inks, plastics, as dopant for the laser marking of plastics and papers, as additive in cosmetic formulations and in the foods and pharmaceuticals sector.

Effect pigments which have a strong silvery lustre effect and are not based on pure metal flakes are of major interest for various applications in surface coatings, plastics, printing inks and cosmetics. Although pigments in this colour range are already on the market, such as, for example, Iriodin® 602 and 612 from Merck, these have, however, no or virtually no sparkle besides the silvery colour.

EP 0 246 523 B1 describes pearlescent pigments which have an iron(II) oxide-containing layer, where this may consist, inter alia, of $FeTiO_3$ (ilmenite). Silvery, non-metallic effect pigments are thus accessible. EP 0 681 009 A2 describes the use of ilmenite-containing interference pigments for the production of counterfeiting-proof securities and packaging. WO 97/43348 A1 describes titanate-containing pearlescent pigments whose inner layer consists of titanium dioxide flakes. WO 2004/099319 A2 describes interference pigments having high hiding power, where at least one $FeTiO_3$-containing layer has been applied to a flake-form, inorganic substrate and the $FeTiO_3$ content, based on the total weight of the layer, is 8-100% by weight and the pigments may have strong silver-coloured effects. WO 2012/130776 A1 describes highly lustrous silver-coloured pigments having high hiding power and a metallic appearance which are based on a non-metallic flake-form synthetic substrate and whose content of iron compounds in the pigment is less than 5.0% by weight, based on the total weight of the pigment.

The non-metallic effect pigments described in the prior art have the disadvantage that, depending on the composition of the layers, they may have a silvery colour, but they exhibit no or only slight sparkle.

The object of the present invention is to provide effect pigments which both exhibit a very strong silver-coloured effect with high lustre and also have high sparkle. Furthermore, it should be possible to prepare the effect pigments by means of a simple process.

Surprisingly, it has now been found that the covering of $Al_2O_3$ flakes having a precisely defined particle size with at least two highly refractive coatings comprising titanium dioxide and $FeTiO_3$ (ilmenite) results in silver-coloured effect pigments which are distinguished not only by their pure and silvery mass tone together with strong lustre, but also by their high sparkle effect.

In contrast to the silvery or silver-grey effect pigments from the prior art, the pigments according to the invention exhibit

- a pure silvery mass tone
- very bright and strong lustre
- a strong sparkle effect and
- high hiding power.

The present invention therefore relates to effect pigments which are distinguished by the fact that $Al_2O_3$ flakes having a thickness of <500 nm with an equivalence diameter distribution ($D_{90}$) according to which 90% of the particles are in the range from 5-45 µm have on the surface two highly refractive coatings having a refractive index n of ≥1.9, where the layers consist of titanium dioxide and ilmenite ($FeTiO_3$) or $TiO_2/Fe_2O_3$ and $FeTiO_3$.

The invention furthermore relates to a process for the preparation of the pigments according to the invention.

The present invention likewise relates to the use of the effect pigments according to the invention in paints, automotive paints, industrial coatings, automotive refinish paints, powder coatings, printing inks, plastics, button pastes, ceramic materials, glasses, for coating seed, as additive for the laser welding of plastics, as dopant in the laser marking or in the laser welding of plastics and papers, as additive for colouring in the foods and pharmaceuticals sector and in cosmetic formulations. The pigments according to the invention are furthermore also suitable for the preparation of pigment preparations and for the preparation of dry preparations, such as, for example, granules, chips, pellets, briquettes, etc. The dry preparations are suitable, in particular, for printing inks and for cosmetic formulations.

Essential features for the silvery effect pigments according to the invention are the base substrate and the layer sequence on the substrate.

In order to achieve a strong sparkle effect, precise setting of the particle size of the starting substrate is important. Sparkle in this application is taken to mean an intense glitter effect.

$Al_2O_3$ flakes and the production thereof are described in detail in the literature. Thus, for example, $Al_2O_3$ flakes are known from the Japanese patent applications JP 72572/1991 and JP 39362/1992.

U.S. Pat. No. 5,702,519 discloses $TiO_2$-doped $Al_2O_3$ flakes which have a thickness of <1 µm and a form factor (aspect ratio: diameter/thickness) of >20.

WO 2006/101306 A1 and WO 2008/026829 A1 disclose zinc-doped $Al_2O_3$ flakes.

Suitable $Al_2O_3$ flakes as substrate for the effect pigments according to the invention may be doped or undoped.

If they are doped, the doping is preferably $TiO_2$, $ZrO_2$, $SiO_2$, $In_2O_3$, $SnO_2$, or ZnO or mixtures thereof. The $Al_2O_3$ substrate is preferably undoped or doped with $TiO_2$.

If the $Al_2O_3$ substrate is doped, the proportion of the doping is preferably <5%, in particular 0.05-3%, based on the substrate.

The $Al_2O_3$ flakes are preferably corundum.

Suitable $Al_2O_3$ flakes are preferably doped or undoped α-$Al_2O_3$ flakes, in particular $TiO_2$-doped α-$Al_2O_3$ flakes.

Of particular importance for the sparkle effect is the particle size distribution of the $Al_2O_3$ flakes.

Suitable $Al_2O_3$ flakes for the effect pigments according to the invention have an equivalence diameter distribution according to which 90% of the particles are in the range from 5-45 µm, preferably 5-40 µm.

The $D_{50}$ values are preferably in the range from 15-30 µm, very particularly preferably in the range from 15-25 µm The $D_{10}$ values are preferably in the range from 5-15 µm, very particularly preferably in the range from 6-10 µm.

Throughout the application, the $D_{10}$, $D_{50}$ and $D_{90}$ values are determined using Malvern MS 2000.

The thickness of the $Al_2O_3$ flakes is <500 nm, preferably 150-450 nm and in particular 150-400 nm.

The form factor (aspect ratio: diameter/thickness ratio) of the $Al_2O_3$ flakes is preferably 30-200, in particular 50-150.

The $Al_2O_3$ flakes having the particle sizes defined above are subsequently covered with at least 2 highly refractive layers.

Highly refractive in this application is taken to mean the refractive index n, which is >1.9.

Firstly, a $TiO_2$ layer is applied to the substrate. This highly refractive $TiO_2$ coating generally has layer thicknesses of 15-200 nm, preferably of 20-150 nm and in particular of 20-100 nm.

The titanium dioxide can be present in the highly refractive coating in the rutile or in the anatase modification, it is preferably in the form of rutile. The processes for the preparation of rutile are described in the prior art, for example in U.S. Pat. Nos. 5,433,779, 4,038,099, 6,626,989, DE 25 22 572 C2, EP 0 271 767 B1. A thin tin oxide layer (<10 nm), which serves as additive in order to convert the $TiO_2$ into rutile, is preferably applied to the $Al_2O_3$ flake before the $TiO_2$ precipitation.

The second layer is a coloured layer comprising a mixture of $TiO_2/Fe_2O_3$ and $FeTiO_3$ (ilmenite) or a pure ilmenite layer. It is preferably an ilmenite layer and not a mixed layer comprising $TiO_2/Fe_2O_3$ and $FeTiO_3$. This coloured layer is located directly on the $TiO_2$ layer and generally has layer thicknesses of 5-100 nm, preferably of 8-80 nm and in particular of 8-50 nm.

Layer or coating in this application is taken to mean the complete covering of the substrate or of the first layer.

The effect pigments according to the invention can be prepared relatively easily.

The covering of the $Al_2O_3$ flakes is preferably carried out by wet-chemical methods, where the wet-chemical coating methods developed for the preparation of pearlescent pigments can be used. Methods of this type are described, for example, in DE 14 67 468, DE 19 59 988, DE 20 09 566, DE 22 14 545, DE 22 15 191, DE 22 44 298, DE 23 13 331, DE 25 22 572, DE 31 37 808, DE 31 37 809, DE 31 51 343, DE 31 51 354, DE 31 51 355, DE 32 11 602, DE 32 35 017 or also in further patent documents and other publications known to the person skilled in the art. Furthermore, the coating of the substrates can also be carried out in a fluidised-bed reactor by gas-phase coating, where, for example, the methods proposed in EP 0 045 851 A1 and EP 0 106 235 A1 for the preparation of pearlescent pigments can be used correspondingly.

The covering of the $Al_2O_3$ flakes with optionally tin oxide and subsequently with titanium dioxide and ilmenite or a $TiO_2/Fe_2O_3$ mixture is preferably carried out by wet-chemical methods, in particular by the chloride or sulfate process.

The effect pigments according to the invention are generally prepared by suspending the $Al_2O_3$ flakes in water and adding one or more hydrolysable tin, titanium and iron salts at a pH which is suitable for hydrolysis, which is selected so that the metal oxides or metal oxide hydrates precipitated directly onto the flakes without significant secondary precipitations occurring. The pH is usually kept constant by simultaneous metered addition of a base and/or acid. After filtration and washing, the coated substrates are dried firstly for 1-5 h at temperatures of 50-150° C., preferably at 80-120° C., and subsequently calcined at 500 to 1200° C., preferably at 500-1000° C., in particular at 500-800° C., for 0.5-5 h, preferably for 0.5-2 h, under reduced conditions, preferably under forming gas ($N_2/H_2$).

The composition of the $FeTiO_3$-containing layer is adjusted through the molar ratio of the water-soluble, inorganic titanium and iron compounds to be employed for the coating, in each case calculated as $TiO_2$ and $Fe_2O_3$. The molar ratio of the titanium and iron compounds employed, in each case calculated as $TiO_2$ and $Fe_2O_3$, is preferably 1:0.1 to 1:0.6, in particular 1:0.25 to 1:0.5.

The resultant effect pigments having the two highly refractive layers are distinguished by pure silvery colours, high lustre, a strong sparkle effect and high hiding power.

In order to increase the light, water and weather stability and/or to improve the wettability and/or compatibility, it is frequently advisable, depending on the area of application, to subject the finished silver-white effect pigment to inorganic or organic post-coating or post-treatment. Suitable post-coatings or post-treatments are the processes described, for example, in German patent 22 15 191, DE-A 31 51 354, DE-A 32 35 017 or DE-A 33 34 598. This post-coating further increases the chemical stability or simplifies handling of the pigment, in particular incorporation into various media. In order to improve the wettability, dispersibility and/or compatibility with the application media, functional coatings comprising $Al_2O_3$ or $ZrO_2$ or mixtures or mixed phases thereof may be applied to the pigment surface. Furthermore, organic or combined organic/inorganic post-coatings are possible, for example with silanes, as described, for example, in DE 10348174, EP 0090259, EP 0 342 533, EP 0 632 109, EP 0 888 410, EP 0 634 459, EP 1 203795, WO 94/01498, WO 96/32446, WO 99/57204, WO 2004/092284, U.S. Pat. Nos. 5,759,255, 5,571,851, WO 01/92425 or in J. J. Ponjeé, Philips Technical Review, Vol. 44, No. 3, 81 ff. and P. H. Harding J. C. Berg, J. Adhesion Sci. Technol. Vol. 11 No. 4, pp. 471-493. The post-coating includes merely a proportion by weight of 0.1 to 5% by weight, preferably 0.5 to 3% by weight, based on the effect pigment.

Since the silver-coloured effect pigments according to the invention exhibit a strong sparkle effect besides bright and strong lustre, particularly effective effects can be achieved with them in the various application media.

The effect pigments according to the invention can be employed in the usual manner for the pigmenting of paints, coatings, printing inks, plastics, cosmetic formulations, ceramic materials, paper and glasses and in the various security applications. Furthermore, the pigments according to the invention are also suitable for the laser marking of paper and plastics, for applications in the agricultural sector, and for the preparation of pigment preparations, such as, for example, pearlets, pastes and dry preparations, such as, for example, pellets, granules, chips, etc., which are preferably used in printing inks and paints. The pigments according to the invention are particularly suitable for use in automotive, automotive refinish and industrial paints. They can likewise be employed in a multiplicity of the known binders used in paint systems and can be used both in water-based systems and also in solvent-based systems.

It goes without saying that, for the various applications, the effect pigments according to the invention can also advantageously be used in the form of a mixture with organic dyes, organic pigments or other pigments, such as, for example, transparent and opaque white, coloured and black pigments, and with flake-form iron oxides, organic pigments, holographic pigments, LCPs (liquid crystal polymers), and conventional transparent, coloured and black lustre pigments based on metal oxide-coated mica and $SiO_2$ flakes, etc. The effect pigments can be mixed with commercially available pigments and fillers in any weight ratio. The ratio is preferably 1:1 to 9:1. If the effect pigments according to the invention are mixed with fillers, the mixing ratio can also be 99:1 to 1:99.

In the various applications, the effect pigment according to the invention can also be combined with further colorants of any type, for example organic and/or inorganic absorption pigments and dyes, multilayered interference pigments, such as, for example, Timiron®, Sicopearl® (BASF AG), ChromaFlair® (Flex Products Inc.), BiOCl pigments, pearl essence or metal pigments, for example from Eckart. No limits are set here for the mixing ratios and concentrations.

The effect pigments according to the invention are compatible with a multiplicity of colour systems, preferably from the area of paints, coatings and printing inks. For the production of printing inks for, for example, gravure printing, flexographic printing, offset printing, offset overprinting, a multiplicity of binders, in particular water-soluble grades, as marketed, for example, by BASF, Marabu, Pröll, Sericol, Hartmann, Gebr. Schmidt, Sicpa, Aarberg, Siegberg, GSB-Wahl, Follmann, Ruco or Coates Screen INKS GmbH, are suitable. The printing inks may be water-based or solvent-based. Furthermore, the effect pigments according to the invention are also suitable for the laser marking of paper and plastics, and for applications in the agricultural sector, for example for greenhouse sheeting, and, for example, for the colouring of tent awnings.

The effect pigments according to the invention can be used for the pigmenting of surface coatings, printing inks, plastics, agricultural sheeting, seed coating, button pastes, medicament coatings or cosmetic formulations, such as lipsticks, nail varnishes, compact powders, shampoos, soaps, loose powders and gels. The concentration of the pigment in the application system to be pigmented is generally between 0.1 and 70% by weight, preferably between 0.1 and 50% by weight and in particular between 0.5 and 10% by weight, based on the total solids content of the system. It is generally dependent on the specific application.

In plastics comprising the effect pigments according to the invention, preferably in amounts of 0.01 to 50% by weight, in particular 0.1 to 7% by weight, particularly pronounced silver and sparkle effects can be achieved.

In the surface coatings sector, in particular in automotive paints, the effect pigments according to the invention are also employed for 3-coat systems in amounts of 0.1-20% by weight, preferably 1 to 10% by weight.

In surface coatings, the effect pigments according to the invention have the advantage that the target gloss is achieved by a one-coat finish (one-coat system or base coat in 2-coat systems). Compared with finishes which comprise, for example, a multilayered mica-based pigment or a conventional pearlescent pigment based on a substrate having a broad thickness distribution instead of the effect pigments according to the invention, finishes comprising the pigment according to the invention exhibit a clearer depth effect and a more highly pronounced silver, lustre and sparkle effect.

The effect pigments according to the invention can also advantageously be employed in decorative and care cosmetics. The use concentration extends from 0.01% by weight in shampoos to 100% by weight in the case of loose powders. In the case of a mixture of the pigments with fillers, preferably with spherical fillers, such as, for example, $SiO_2$, the concentration can be 0.01-70% by weight in the formulation. The cosmetic products, such as, for example, nail varnishes, compact powders, shampoos, loose powders and gels, are distinguished by particularly interesting colour effects and high lustre.

The pigments according to the invention can furthermore be mixed with commercially available fillers. Fillers which may be mentioned are, for example, natural and synthetic mica, nylon powder, pure or filled melamine resins, talc, glasses, kaolin, oxides or hydroxides of aluminium, magnesium, calcium, zinc, BiOCl, barium sulfate, calcium sulfate, calcium carbonate, magnesium carbonate, carbon, and physical or chemical combinations of these substances. There are no restrictions regarding the particle shape of the filler. It can be, for example, flake-form, spherical or needle-shaped in accordance with requirements.

The effect pigments according to the invention can of course also be combined in the formulations with cosmetic raw materials and assistants of any type. These include, inter alia, oils, fats, waxes, film formers, preservatives and assistants which generally determine the applicational properties, such as, for example, thickeners and rheological additives, such as, for example, bentonites, hectorites, silicon dioxides, Ca silicates, gelatines, high-molecular-weight carbohydrates and/or surface-active assistants, etc.

The formulations comprising the effect pigments according to the invention can belong to the lipophilic, hydrophilic or hydrophobic type. In the case of heterogeneous formulations having discrete aqueous and non-aqueous phases, the effect pigments according to the invention may in each case be present in only one of the two phases or alternatively distributed over both phases.

The pH values of the formulations can be between 1 and 14, preferably between 2 and 11 and particularly preferably between 5 and 8.

No limits are set for the concentrations of the effect pigments according to the invention in the formulation. They can be—depending on the application—between 0.001 (rinse-off products, for example shower gels) and 100% (for example lustre-effect articles for particular applications).

The effect pigments according to the invention may furthermore also be combined with cosmetic active ingredients. Suitable active ingredients are, for example, insect repellents, UV A/BC protective filters (for example OMC, B3, MBC), anti-ageing active ingredients, vitamins and derivatives thereof (for example vitamin A, C, E, etc.), self-tanning agents (for example DHA, erythrulose, inter alia), and further cosmetic active ingredients, such as, for example, bisabolol, LPO, ectoin, emblica, allantoin, bioflavonoids and derivatives thereof.

In the pigmenting of binder systems, for example for paints and printing inks for gravure printing, offset printing or screen printing, or as precursor for printing inks, the use of the effect pigments according to the invention in the form of highly pigmented pastes, granules, pellets, etc., has proven particularly suitable. The effect pigments are generally incorporated into the printing ink in amounts of 2-35% by weight, preferably 5-25% by weight, and in particular 8-20% by weight. Offset printing inks can comprise the pigments in amounts of up to 40% by weight or more. The precursors for the printing inks, for example as a paste or in the form of granules, pellets, briquettes, etc., comprise up to 98% by weight of the pigment according to the invention in addition to the binder and additives. The printing inks comprising the pigments according to the invention exhibit purer hues than with conventional silver pigments. The particle thicknesses of the effect pigments according to the invention are relatively small and therefore bring about particularly good printability.

The effect pigments according to the invention are furthermore suitable for the preparation of flowable pigment preparations and dry preparations, the latter for example in the form of pellets, granules, chips, briquettes, beads, sausages, preferably having particle sizes of 0.1-2 cm, in particular for printing inks, comprising one or more effect pigments according to the invention, binders and optionally one or more additives. The dry preparations can be prepared by all processes known to the person skilled in the art, for example by granulation, spray granulation, spray drying, pelleting, briquetting, etc.

The invention thus also relates to formulations, in particular automotive paints, automotive refinish paints, powder coatings and industrial coatings, comprising the effect pigments according to the invention.

The invention relates, in particular, to formulations which, besides the effect pigments according to the invention, comprise at least one constituent selected from absorbents, astringents, antimicrobial substances, antioxidants, antiperspirants, antifoaming agents, antidandruff active compounds, anti-statics, binders, biological additives, bleaches, chelating agents, deodorants, emollients, emulsifiers, emulsion stabilisers, dyes, humectants, film formers, fragrances, flavours, insect repellents, preservatives, anticorrosion agents, cosmetic oils, solvents, oxidants, vegetable constituents, buffer substances, reducing agents, surfactants, propellant gases, opacifiers, UV filters and UV absorbers, denaturing agents, viscosity regulators, perfume and vitamins.

The following examples are intended to explain the invention, but without limiting it.

All percentages, unless indicated otherwise, are percent by weight.

EXAMPLES

Example 1

100 g of $Al_2O_3$ flakes of particle size 5-40 µm having a thickness of 220-400 nm are heated to 75° C. in 1 l of demineralised water with stirring. The pH of the suspension is subsequently adjusted to 1.8 using 10% hydrochloric acid. This is followed by the metered addition of a 2% tin tetrachloride solution (5.6 g of $SnCl_4$ (50%) dissolved with 17.2 g of 32% HCl and 110 ml of demineralised water), during which the pH is kept constant by simultaneous dropwise addition of 32% sodium hydroxide solution. When the addition is complete, the mixture is stirred for a further 15 min. Addition of 30% titanium tetrachloride solution (68 g of $TiCl_4$ (25%) dissolved in 58.6 g of demineralised water) subsequently follows, during which the pH is kept constant by simultaneous dropwise addition of 32% sodium hydroxide solution. When the addition is complete, the mixture is stirred for a further 15 min.

The pH of the suspension is then set to 2.8 using 32% sodium hydroxide solution. 72.8 g of an $FeCl_3$ solution w=7.0% are subsequently metered in, during which the pH is kept constant by simultaneous dropwise addition of 32% sodium hydroxide solution. When the addition is complete, the mixture is stirred again for a further 15 min. The pH value of pH 5.0 is set using 32% sodium hydroxide solution, and the mixture is stirred again for a further 10 min.

The product is filtered off, washed, dried, calcined at 650° C. under reducing conditions ($N_2/H_2$) for 2 h and sieved through a sieve, giving a bluish silver-coloured effect pigment having high lustre and an intense sparkle effect.

The particle size distribution of the pigment according to Example 1 determined using Malvern MS 2000 gives:
$D_{10}$=8.6 µm
$D_{50}$=18.2 µm
$D_{90}$=33.3 µm

Example 2

100 g of $Al_2O_3$ flakes of particle size 5-40 µm having a thickness of 220-400 nm are heated to 75° C. in 1 l of demineralised water with stirring. The pH of the suspension is subsequently adjusted to 1.8 using 10% hydrochloric acid. This is followed by the metered addition of a 2% tin tetrachloride solution (5.6 g of $SnCl_4$ (50%) dissolved with 17.2 g of 32% HCl and 110 ml of demineralised water), during which the pH is kept constant by simultaneous dropwise addition of 32% sodium hydroxide solution. When the addition is complete, the mixture is stirred for a further 15 min.

A 30% titanium tetrachloride solution (92 g of $TiCl_4$ (25%) dissolved in 79.2 g of demineralised water) is subsequently added, during which the pH is kept constant by simultaneous dropwise addition of 32% sodium hydroxide solution. When the addition is complete, the mixture is stirred for a further 15 min.

The pH of the suspension is then set to 2.8 using 32% sodium hydroxide solution. 72.8 g of an $FeCl_3$ solution w=7.0% are subsequently metered in, during which the pH is kept constant by simultaneous dropwise addition of 32% sodium hydroxide solution. When the addition is complete, the mixture is stirred again for a further 15 min. The pH value of pH 5.0 is set using 32% sodium hydroxide solution, and the mixture is stirred again for a further 10 min.

The product is filtered off, washed, dried, calcined at 650° C. under reducing conditions ($N_2/H_2$) for 2 h and sieved through a sieve, giving a neutral silver-coloured effect pigment having high lustre and an intense sparkle effect.

The particle size distribution of the pigment according to Example 2 determined using Malvern MS 2000 gives:
$D_{10}$=8.8 µm
$D_{50}$=18.5 µm
$D_{90}$=33.5 µm

Example 3

100 g of $Al_2O_3$ flakes of particle size 5-40 µm having a thickness of 220-400 nm are heated to 75° C. in 1 l of demineralised water with stirring. The pH of the suspension is subsequently adjusted to 1.8 using 10% hydrochloric acid. This is followed by the metered addition of a 2% tin tetrachloride solution (5.6 g of $SnCl_4$ (50%) dissolved with 17.2 g of 32% HCl and 110 ml of demineralised water), during which the pH is kept constant by simultaneous dropwise addition of 32% sodium hydroxide solution. When the addition is complete, the mixture is stirred for a further 15 min. A 30% titanium tetrachloride solution (120 g of $TiCl_4$ (25%) dissolved in 103.3 g of demineralised water) is now added, during which the pH is kept constant by simultaneous dropwise addition of 32% sodium hydroxide solution. When the addition is complete, the mixture is stirred for a further 15 min.

The pH of the suspension is subsequently set to 2.8 using 32% sodium hydroxide solution. 72.8 g of an $FeCl_3$ solution w=7.0% are then metered in, during which the pH is kept constant by simultaneous dropwise addition of 32% sodium hydroxide solution. When the addition is complete, the mixture is stirred again for a further 15 min. The pH value of pH 5.0 is set using 32% sodium hydroxide solution, and the mixture is stirred again for a further 10 min.

The product is filtered off, washed, dried, calcined at 650° C. under reducing conditions ($N_2/H_2$) for 2 h and sieved through a sieve, giving a goldish silver-coloured effect pigment having high lustre and an intense sparkle effect.

The particle size distribution of the pigment according to Example 3 determined using Malvern MS 2000 gives:
$D_{10}$=8.9 µm
$D_{50}$=18.6 µm
$D_{90}$=33.6 µm

Examples 4-6: Post-Coating

In order to increase the light, water and/or weather stability or for improved incorporation of the pigments into the respective application medium, the effect pigments of Examples 1-3 are subjected to a post-coating. The post-coating is carried out as described in the following patent applications and patents:

DE 22 15 191, DE 31 51 354, DE 32 35 017, DE 33 34 598, DE10348174, EP 0090259, EP 0 342 533, EP 0632109, EP 0 888 410, EP 1203795, WO94/01498, WO 96/32446, WO 99/57204, WO 02/064682, WO 2004/092284 and U.S. Pat. No. 5,759,255. The proportion of the post-coating in the case of the pigments of Examples 1-3 is in each case 2%, based on the effect pigment.

USE EXAMPLES

Examples A1:—Paint System

90% by weight of Hydroglasur BG/S colourless (waterborne paint from Ernst Diegel GmbH)
10% by weight of bluish silver-coloured effect pigment from Example 1
Painting by spraying on at 80° C.
5 min pre-drying at 80° C.
20 min baking at 180° C.

Example A2 is carried out analogously to Example A1, but the uncoated pigment from Example 1 is replaced by the corresponding post-coated pigment of Example 1.

Example B:—Plastic 1 kg of polystyrene granules are uniformly wetted with 5 g of coupling agent in a tumble mixer. 42 g of effect pigment from Example 2 are then added and mixed for 2 min. These granules are converted into stepped plates having the dimensions 4×3×0.5 cm under conventional conditions in an injection-moulding machine. The stepped plates are distinguished by their pronounced sparkle effect.

The products of Use Examples A1, A2 and B are distinguished by their high lustre, their silver colour and an intense sparkle effect.

The invention claimed is:
1. An effect pigment comprising:
$Al_2O_3$ flakes as substrate having an equivalent diameter distribution according to which 90% of the particles are in the range from 5-45 µm, the $Al_2O_3$ flakes as substrate being doped with $TiO_2$, $ZrO_2$, $SiO_2$, $In_2O_3$, $SnO_2$, or ZnO or mixtures thereof,
wherein the pigment has two highly refractive layers each having a refractive index n>1.9 on the substrate,
wherein one of said two highly refractive layers consists of titanium dioxide and the other of said two highly refractive layers contains ilmenite ($FeTiO_3$) or $TiO_2$/$Fe_2O_3$ and $FeTiO_3$,
wherein said one of said two highly refractive layers consisting of titanium dioxide has a layer thickness of 15-200 nm, and
wherein said effect pigment is a silver-colored effect pigment.
2. The effect pigment according to claim 1, wherein the form factor (aspect ratio: diameter/thickness ratio) of the $Al_2O_3$ flakes is 30-200.
3. The effect pigment according to claim 1, wherein the $Al_2O_3$ flakes are corundum.
4. The effect pigment according to claim 1, wherein the $Al_2O_3$ flakes are doped with $TiO_2$.
5. The effect pigment according to claim 1, wherein the proportion of the doping is <5%, based on the substrate.
6. The effect pigment according to claim 1, wherein the other of said two highly refractive layers is an $FeTiO_3$ layer.
7. The effect pigment according to claim 6, wherein the highly refractive layer consisting of titanium dioxide is in the rutile modification.
8. The effect pigment according to claim 1, wherein the other of said two highly refractive layers has a thickness of 5-100 nm.
9. The effect pigment according to claim 1, wherein the proportion of the doping is 0.05-3%, based on the substrate.
10. The effect pigment according to claim 1, wherein the $Al_2O_3$ flakes have a $D_{50}$ value in the range from 15-30 µm.
11. The effect pigment according to claim 1, wherein the $Al_2O_3$ flakes have a $D_{50}$ value in the range from 15-25 µm.
12. The effect pigment according to claim 1, wherein the $Al_2O_3$ flakes have a $D_{10}$ value in the range from 5-15 µm.
13. The effect pigment according to claim 1, wherein the $Al_2O_3$ flakes have a $D_{10}$ value in the range from 6-10 µm.
14. The effect pigment according to claim 1, wherein the form factor (aspect ratio: diameter/thickness ratio) of the $Al_2O_3$ flakes is 50-150.
15. The effect pigment according to claim 1, wherein said one of said two highly refractive layers consisting of titanium dioxide is applied to the substrate, and the other of said two highly refractive layers is a colored layer which is applied to said layer consisting of titanium dioxide and is a mixture of $TiO_2$/$Fe_2O_3$ and $FeTiO_3$ or is a pure ilmenite layer, said colored layer having a layer thickness of 5-100 nm.
16. The effect pigment according to claim 15, wherein said layer consisting of titanium dioxide has a layer thickness of 20-150 nm and said colored layer has layer thicknesses of 8-80 nm.
17. The effect pigment according to claim 15, wherein said layer consisting of titanium dioxide has a layer thickness of 20-100 nm and said colored layer has layer thicknesses of 8-50 nm.
18. A formulation comprising one or more effect pigments according to claim 1.
19. The formulation according to claim 18, further comprising at least one constituent selected from absorbents, astringents, antimicrobial substances, antioxidants, antiperspirants, antifoaming agents, antidandruff active compounds, antistatics, binders, biological additives, bleaches, chelating agents, deodorants, emollients, emulsifiers, emulsion stabilizers, dyes, humectants, film formers, fragrances, flavors, insect repellents, preservatives, anticorrosion agents, cosmetic oils, solvents, oxidants, vegetable constituents, buffer substances, reducing agents, surfactants, propellant gases, opacifiers, UV filters and UV absorbers, denaturing agents, viscosity regulators, perfume and vitamins.
20. A pigment preparation or paste comprising one or more binders, optionally one or more additives, and one or more effect pigments according to claim 1.
21. A dry preparation comprising one or more effect pigments according to claim 1, wherein said preparation is in the form of pellets, granules, chips, briquettes, beads- or sausages.
22. A process for the preparation of the effect pigments according to claim 1, said process comprising forming said layers by coating the $Al_2O_3$ flakes by a wet-chemical method of precipitation from metal salts in aqueous medium, and subsequent calcining the coated flakes in a reducing gas atmosphere.
23. An effect pigment comprising:
$Al_2O_3$ flakes as substrate having an equivalent diameter distribution according to which 90% of the particles are in the range from 5-45 µm, the $Al_2O_3$ flakes as substrate being doped with $TiO_2$, $ZrO_2$, $SiO_2$, $In_2O_3$, $SnO_2$, or ZnO or mixtures thereof, wherein the pigment has two highly refractive layers each having a refractive index n>1.9 on the substrate, wherein one of said two highly refractive layers consists of titanium dioxide and the other of said two highly refractive layers contains ilmenite ($FeTiO_3$) or $TiO_2$/$Fe_2O_3$ and $FeTiO_3$, wherein said one of said two highly refractive layers consisting of titanium dioxide has a layer thickness of 15-200 nm, wherein said other of said two highly refractive layers has layer thicknesses of 5-100 nm, wherein the thickness of the $Al_2O_3$ flakes is 150-450 nm and the form factor (aspect ratio: diameter/thickness ratio) of the $Al_2O_3$ flakes is 30-200, and wherein the $Al_2O_3$ flakes have a $D_{50}$ value in the range from 15-30 µm and a $D_{10}$ value in the range from 5-15 µm, and wherein said effect pigment is a silver-colored effect pigment.

* * * * *